United States Patent [19]

Sera et al.

[11] 4,028,320
[45] June 7, 1977

[54] METHOD OF HARDENING GELATIN USING SULFONYL COMPOUNDS

[75] Inventors: Hidefumi Sera; Kameji Nagao; Tsumoru Ishii, all of Minami-ashigara, Japan

[73] Assignee: Fujii Photo Film Co., Ltd., Minami-ashigara, Japan

[22] Filed: Apr. 26, 1976

[21] Appl. No.: 680,416

[30] Foreign Application Priority Data

Apr. 25, 1975 Japan .............................. 50-50500

[52] U.S. Cl. .................................. 260/117; 96/111; 106/125
[51] Int. Cl.² ......................................... C09H 7/00
[58] Field of Search ................... 260/117; 96/111; 106/125

[56] References Cited

UNITED STATES PATENTS

| | | | |
|---|---|---|---|
| 3,132,945 | 5/1964 | Ryan | 260/117 X |
| 3,455,892 | 7/1969 | Froehlich | 260/117 |
| 3,490,911 | 1/1970 | Burness et al. | 96/111 |
| 3,642,486 | 2/1972 | Burness et al. | 260/117 X |
| 3,687,707 | 8/1972 | Graham | 260/117 X |
| 3,689,274 | 9/1972 | Sobel et al. | 96/111 |
| 3,839,042 | 10/1974 | Silverman et al. | 96/111 X |
| 3,841,872 | 10/1974 | Burness et al. | 260/117 X |
| 3,868,257 | 2/1975 | Horii et al. | 260/117 X |

*Primary Examiner*—Howard E. Schain
*Attorney, Agent, or Firm*—Sughrue, Rothwell, Mion, Zinn & Macpeak

[57] ABSTRACT

A method of hardening gelatin which comprises adding thereto a compound of the following general formula (I):

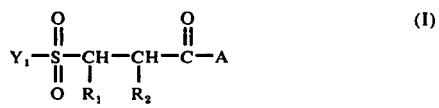

in which $Y_1$ is $CH_2=CH-$, $ClCH_2-CH_2-$, $BrCH_2-CH_2-$, $CH_3COO-CH_2CH_2-$ or $ClCH_2COO-CH_2CH_2-$, $R_1$ and $R_2$ are H or $CH_3$, but both of them are not $CH_3$ at the same time, and A is one of the following groups:

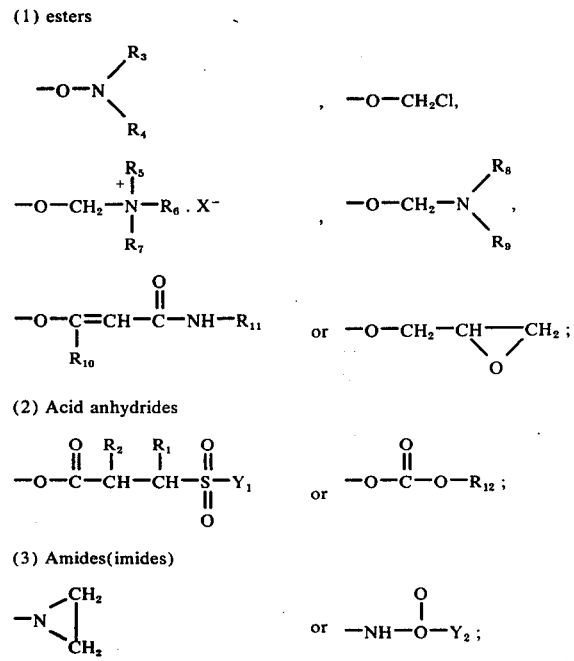

in which both $R_3$ and $R_4$ were acyl groups or at least one of them is an acyl group other than when $R_3$ and $R_4$ form a benzotriazole ring, and when one of $R_3$ and $R_4$ is an acyl group, the other is H or an alkyl group containing at most 4 carbon atoms; and wherein in any case, $R_3$ and $R_4$ may form a saturated or unsaturated carbocyclic or heterocyclic ring in combination with the nitrogen atom to which they are attached; $R_5$, $R_6$ and $R_7$ are alkyl groups containing at most 4 carbon atoms, and may form a saturated or unsaturated ring, or may form a bicyclo ring; $X^-$ is an acid anion; $R_8$ and $R_9$ are a saturated or unsaturated carbocyclic or heterocyclic ring which combine with the nitrogen atom to which they are attached; $R_{10}$ is an alkyl or aryl group containing at most 6 carbon atoms; $R_{11}$ is an alkyl group containing at most 3 carbon atoms; $R_{12}$ is an alkyl, aryl or aralkyl group containing at most 7 carbons atoms; $Y_2$ is $CH_2=CH-$, $ClCH_2-CH_2-$, $Br-CH_2CH_2-$, $CH_3COO-CH_2CH_2-$, or $ClCH_2COO-CH_2CH_2-$, and $Y_1$ is as earlier defined.

8 Claims, No Drawings

METHOD OF HARDENING GELATIN USING SULFONYL COMPOUNDS

BACKGROUND OF THE INVENTION

1. Field of the Invention

The present invention relates to a method of hardening gelatin, more particularly, it relates to a method of hardening gelatin used for silver halide photographic materials.

2. Description of the Prior Art

Gelatin is used as binder for many photographic materials. For example, gelatin is used as the main constituent of a silver halide sensitive emulsion layer, emulsion protective layer, filter layer, intermediate layer, anti-halation layer, backing layer, film base subbing layer and baryta layer.

These photographic materials containing gelatin are treated with various aqueous solutions having different pH's and temperatures. Since a layer containing gelatin not treated with a hardening agent has gelatin-like properties, it has poor water resistance and swells excessively in an aqueous solution, so that the mechanical strength is greatly lowered, and, in an extreme case, the gelatin layer is sometimes dissolved, particularly when in an aqueous solution having a high temperature of above 30° C or a highly alkaline aqueous solution.

These properties are fatal defects as physical properties of photographic material layers.

In order to raise the water resistance, heat resistance and scratch resistance of a gelatin layer by hardening, many compounds are known which are used in the production of photographic materials. Examples are formaldehyde, glutaraldehyde and like aldehyde type compounds; compounds having a reactive halogen as described in U.S. Pat. No. 3,288,775 and so on; compounds containing a reactive ethylenic unsaturated bonding as described in U.S. Pat. No. 3,635,718 and so on; aziridine type compounds as described in U.S. Pat. No. 3,017,280; epoxy compounds as described in U.S. Pat. No. 3,091,537; and halogenocarboxyaldehydes such as mucochloric acid, dioxanes such as dihydroxydioxane and dichlorodioxane, or inorganic hardeners such as chromium alum and zirconium sulfate.

However, most of these hardeners have serious defects with regard to photographic properties, the gelatin hardening velocity (film hardening velocity) is not always sufficiently fast, so that film hardening slowly proceeds with the passage of time after the production of the photographic materials (i.e., after-hardening), the photographic properties (e.g., sensitivity and color balance) which are affected by the state of gelatin film hardening are not stabilized and the properties immediately after production vary slowly with the passage of time.

On the other hand, certain kinds of hardeners which have a remarkably high hardening velocity (to thereby prevent after hardening) are known and are called rapid hardeners.

However, most rapid hardeners lead to serious defects in photographic material production steps that a hardening reaction proceeds before film formation (e.g., in a tank or in a coating head for coating before coating of the photographic emulsion on a support) when the rapid hardener is added to a gelatin solution so that the viscosity of the gelatin solution is raised and coating of the photographic emulsion becomes very difficult.

SUMMARY OF THE INVENTION

One object of the present invention is to provide novel hardeners for gelatin.

Another object of the present invention is to provide gelatin hardeners which have a hardening velocity sufficient to give photographic materials having stable characteristics (i.e., the change with the passage of time is greatly reduced with regard to swelling velocity, swelling ratio and the resulting sensitivity and color balance of the photographic materials) and which have such a stability that the viscosity of the gelatin solution is not increased until film formation (after adding of the hardeners to the gelatin solution).

Still another object of the present invention is to provide novel hardeners for gelatin which impart excellent water resistance, heat resistance and scratch resistance to the photographic materials without adversely affecting the quality of the photographic materials.

These objects can be attained by adding one or more compounds of the following general formula (I) to gelatin.

$$Y_1-\underset{\underset{O}{\|}}{\overset{\overset{O}{\|}}{S}}-\underset{R_1}{\overset{}{CH}}-\underset{R_2}{\overset{}{CH}}-\overset{\overset{O}{\|}}{C}-A \quad (I)$$

where $Y_1$ represents $CH_2=CH-$, $ClCH_2CH_2-$, $BrCH_2CH_2-$, $CH_3COO-CH_2CH_2-$, or $ClCH_2COO-CH_2CH_2-$, $R_1$ and $R_2$ represents H or $CH_3$ but are not simultaneously $CH_3$, and A represents the following esters, acid anhydrides or amides(imides):

(1) esters

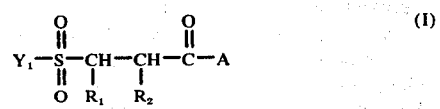

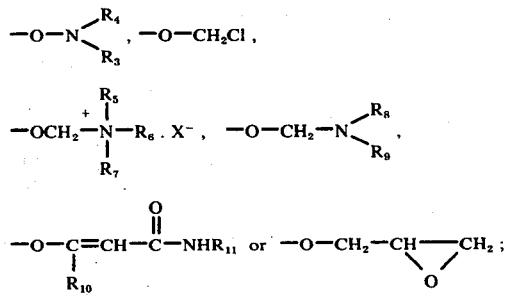

(2) Acid anhydrides

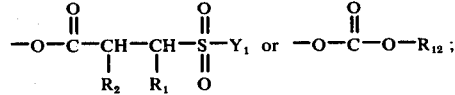

(3) Amides (imides)

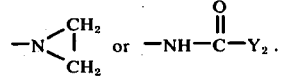

In the above formulae, both $R_3$ and $R_4$ are acyl groups or at least one of $R_3$ and $R_4$ is an acyl group other than in the case when $R_3$ and $R_4$ form a benzotriazole ring, with preferred acyl groups including those derived from a carboxylic acid (preferably an aliphatic carboxylic acid) and containing 2 to 10 carbon atoms. When forming a benzotriazole ring, $R_3$ and $R_4$ form a condensed ring, the nitrogen atom to which $R_3$ and $R_4$ are attached is a nitrogen atom at the 1-position, and the 4-, 5- or 6-position may have a substituent such as, for example, a halogen atom, e.g., chlorine, bromine, etc., an alkoxy group of from 1 to 4 carbon atoms, e.g., methoxy, ethoxy, etc., an acylamido group of 2 to 4 carbon atoms, e.g., acetamide, butyramide, etc., a carbamoyl group, e.g., carbamoyl, a mono- or di-alky substituted carbamoyl group, wherein the alkyl moieties most preferably have from 1 to 4 carbon atoms each, for example, methyl carbamoyl, diethylcarbamoyl, etc., a sulfamoyl group, e.g., sulfamoyl, a mono or di-alkyl substituted sulfamoyl group wherein the alkyl moieties each preferably have 1 to 4 carbon atoms, e.g., methylsulfamoyl, diethylsulfamoyl, etc., a carboxy group, a sulfo group, or salts thereof, for example, salts such as an alkali metal salt, e.g., sodium or potassium, etc., or a tertiary ammonium salt, e.g., triethyl ammonium, etc.

When $R_3$ and $R_4$ are acyl groups, $R_3$ and $R_4$ may form a carbocyclic or heterocyclic ring, which can be saturated or unsaturated. Most preferably $R_3$ and $R_4$ are the residues necessary to form a 5- or 6-membered ring which can be condensed with an aromatic ring such as benzene, naphthalene, etc., wherein preferred heterocyclic rings contain at least one nitrogen, oxygen or sulfur atom as a hetero atom. Examples of preferred rings include succinimide, maleinimide, phthalimido, hydantoinyl, oxazolidinyl, thiazolidinyl, and the like.

When one of $R_3$ and $R_4$ is an acyl group, the other represents H, $Ch_3$, $C_2H_5$ or a like $C_{1-4}$ lower alkyl group.

$R_5$, $R_6$ and $R_7$ are $C_{1-4}$ lower alkyl groups and two or three of them in combination may form a ring. That is, when two of them form a ring, each forms a saturated ring such as an N-methylpiperidinium residue or an N-ethylmorpholinium residue in combination with the nitrogen atom. When three of them form a ring, each forms an unsaturated ring such as a pyridinium residue or a saturated bicyclo ring such as a 1-azonia-4-azabicyclo(2,2,2)-octane residue, in combination with the nitrogen atom. In this case $X^-$ is an organic or inorganic acid anion, more particularly a water-soluble acid anion, e.g., $Cl^-$, $Br^-$, $HSO_4^-$, $NO_3^-$, $CH_3SO_3^-$, $SO_3^-$, $CH_3-$, $-SO_3^-$, etc.

$R_8$ and $R_9$ are residues which form a ring, including a carbocylic or heterocyclic ring, which can be saturated or unsaturated. Most preferably $R_8$ and $R_9$ are the residues necessary to form a $5^-$ or 6-membered ring which can be condensed with an aromatic ring such as benzene, naphthelene, etc. wherein preferred heterocyclic rings contain at least one nitrogen, oxygen or sulfur atom as a hetero atom. Examples of most preferred rings include succinimide, maleinimide, phthalimido, hydantoinyl, oxazolidinyl, thiazolidinyl, and the like.

$R_{10}$ represents an alkyl group or an aryl group, each containing at most 6 carbon atoms.

$R_{11}$ represents an alkyl group containing at most 3 carbon atoms.

$R_{12}$ represents an alkyl group, an aryl group or an aralkyl group, each containing at most 7 carbon atoms.

$Y_2$ represents $CH_2=CH-$, $ClCH_2CH_2-$, $BrCH_2CH_2-$, $CH_3COO-$ $CH_2CH_2-$, or $ClCH_2COO-CH_2CH_2-$.

$Y_1$ is as earlier defined.

DETAIL DESCRIPTION OF THE INVENTION

The compounds of the present invention are all novel compounds and can be prepared in good yield by known reactions. For example, they can be prepared by the reaction of 3-(β-chloroethanesulfonyl)propionyl chloride, 3-(β-chloroethanesulfonyl)-3-methylpropionyl chloride or 3-(β-chloroethanesulfonyl)-2-methylpropionyl chloride and the corresponding compounds such as N-hydroxysuccinimide, paraformaldehyde, ethyleneimine, glycidol and chloroacetamide.

3-(β-Chloroethanesulfonyl)propionyl chloride, 3-(β-chloroethanesulfonyl)-3-methylpropionyl chloride and 3-(β-chloroethanesulfonyl)-2-methylpropionyl chloride are novel compounds and can be prepared by the addition reaction of acrylic acid, methacrylic acid or crotonic acid with a reaction product of β-chloroethanesulfonyl chloride sodium sulfite and sodium hydroxide, to produce a free acid, and then halogenating this free acid with thionyl chloride or phosphorus pentachloride.

The reactions involved are based upon conventional mechanisms, and conventional conditions can be used, for example, typically the reactants are used at a molar ratio of 1:1 (theoretical ratio), reaction is conducted at normal pressure and at a temperature of from 0° to about 100° C, with the time of reaction not being restricted in any special fashion.

Examples of the compounds used in the present invention are given below, but the present invention is not limited to these examples.

Compound 1

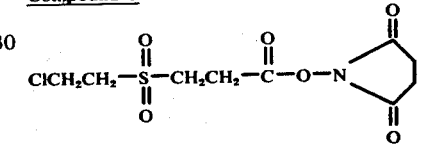

Compound 2

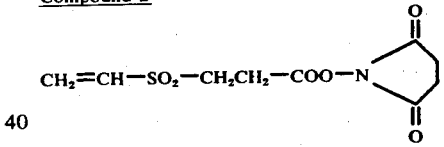

Compound 3

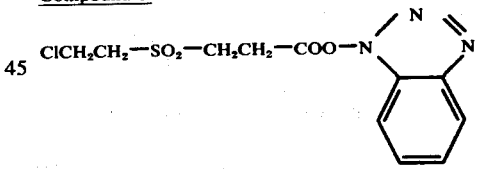

Compound 4

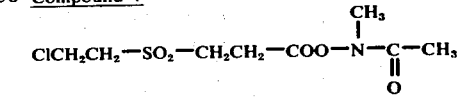

Compound 5

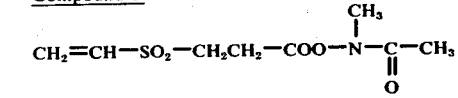

Compound 6

Compound 7

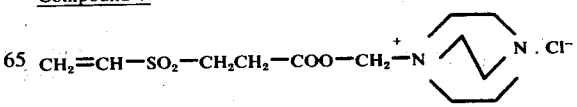

Compound 8

-continued

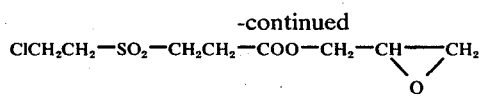

Compound 9

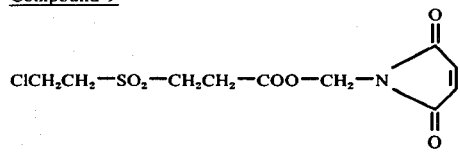

Compound 10

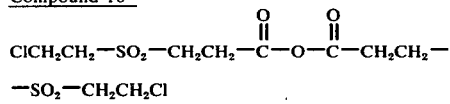

Compound 11

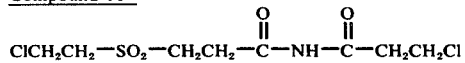

Compound 12

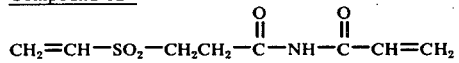

Compound 13

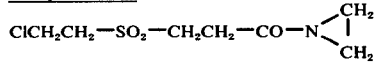

Among these compounds, compounds 1, 2, 4, 5, 7, 11 and 12 are preferably used, and particularly compounds 2, 5 and 12 are most preferred.

The hardening reaction takes place smoothly and after hardening does not occur with the hardeners of the present invention, so that the photographic material produced using the present hardeners have a constant gelatin film strength from immediately after their production. Accordingly, no difference in apparent sensitivity and color balance due to differences of the diffusion velocity of the developer is observed between the photographic material immediately after production and the photographic material after the passage of time.

In addition, the hardener of the present invention has a preferred hardening velocity in spite of the fact that after hardening does not take place, and, therefore, the viscosity of the gelatin solution is not raised until the formation of the film after addition of the present hardener to the gelatin solution, which is very valuable in the mass production of photographic materials. Further, the present hardener does not reduce the effects of other additives such as couplers for color photographic materials through interaction with such additives, nor does it lose its hardening effect through such interaction. Yet further, the present hardener does not adversely affect the photographic properties of the photographic material, (e.g., to cause fogging or a reduction of sensitivity.

The amount of the hardener of the present invention used can be selected freely depending on the desired objective. The amount used is generally in the range of from about 0.05 to about 20 wt.% based on dry gelatin, preferably in the range of from 0.1 to 10 wt.%, same basis. When the hardener of the present invention is used in an amount of more than about 20 wt% based on the dry gelatin, the gelatin solution is gelated and hardened, so that it is impossible to mold using the gelatin aqueous solution, e.g., it is impossible to form a film by coating or spray coating. On the other hand, with the use amount of less than about 0.05 wt%, a sufficient hardening cannot be obtained even after drying, and the film strength is insufficient, though it is possible to mold using the gelatin aqueous solution. In the above range of the amount used the property of hardening gelatin smoothly, which is the feature of the hardener of the present invention, can be exerted satisfactorily.

The hardeners of the present invention can be used alone or as mixtures of two or more hardeners of the present hardeners. Further, the hardeners of the present invention can be used in combination with other known hardeners. Known hardeners are, for example, formaldehyde, glutaraldehyde and like aldehyde type compounds; diacetyl, cyclopentadione and like ketone compounds; bis(2-chloroethylurea), 2-hydroxy-4,6-dichloro-1,3,5-triazine; compounds containing reactive halogen, divinylsulfone, 5-acetyl-1,3-diacryloylhexahydro-1,3,5-triazine as described in U.S. Pats. Nos. 3,288,775 and 2,732,303 and British Pats. Nos. 974,723 and 1,167,207; compounds containing reactive olefine, N-hydroxymethylphthalimide as described in U.S. Pats. Nos. 3,635,718 and 3,232,763 and British Pat. No. 994,869; N-methylol compounds as described in U.S. Pats. Nos. 2,732,316 and 2,586,168; isocyanates as described in U.S. Pat. No. 3,103,437; aziridine compounds as described in U.S. Pats. Nos. 3,017,280 and 2,983,611; acid derivatives as described in U.S. Pats. Nos. 2,725,294 and 2,725,295; carbodiimide type compounds as described in U.S. Pat. No. 3,100,704; epoxy compounds as described in U.S. Pat. No. 3,091,537; isoxazole type compounds as described in U.S. Pats. Nos. 3,321,313 and 3,543,292; halogenocarboxyaldehydes such as mucochloric acid, dioxane derivatives such as dihydroxydioxane and dichlorodioxane; and inorganic hardeners such as chromium alum and zirconium sulfate. Instead of above compounds the hardeners of the present invention can be used in combination with precursors of said compounds, such as alkali metal bisulfite aldehyde adducts, methylol derivatives of hydantoin and primary fatty nitroalcohols, etc. When using the hardener of the present invention in combination with other hardeners, the amount of the hardener (s) of the present invention used can be selected freely depending on the object and the effect.

In using the hardener of the present invention for photographic materials, a silver halide emulsion can be prepared by mixing a water-soluble silver salt (e.g., silver nitrate) solution and a water-soluble halide (e.g., potassium bromide) solution in the presence of a water-soluble polymer (e.g., gelatin) solution. Useful silver halides include silver chloride, silver bromide and mixed silver halides such as silver chlorobromide, silver iodobromide and silver chloroiodobromide.

The form of the silver halide particles may be any of a cubic, octahedral and mixed system. The particle size and average particle size distribution are not particularly limited.

These silver halide particles are prepared by known conventional procedures, e.g., a single or double jet method, a controlled double jet method and the like. Further, two or more kinds of silver halide emulsions which have been separately prepared may be mixed.

The crystal structure of the silver halide particle may be uniform from the exterior to the interior, it may be stratiform where the outer layer and an inner layer are heterogeneous or may be of the conversion type as shown in British Pat. No. 635,841 and U.S. Pat. No. 3,622,318. Further, it may be of the type which forms a latent image principally on its surface or may be of the inner latent image type which forms a latent image in the inside of the particle. These photographic emulsions are described in Mees, *The Theory of the Photographic Process*, MacMillian; P. Glafkides, *Chimie Photographique*, Paul Montel (1957) and the like, and can be prepared by the known ammonia method, neutral method, acid method and the like.

After the formation of such silver halide particles, water-soluble salt by-products (e.g., potassium nitrate when producing silver bromide from silver nitrate and potassium bromide) are removed from the system by water-washing, and then heating is conducted in the presence of a chemical sensitizer such as sodium thiosulfate, N,N,N'-trimethylthiourea, a thiocyanate complex salt of monovalent gold, a thiosulfuric acid complex salt, stannous chloride or hexamethylenetetramine without making the particle larger to thereby raising the sensitivity. Such a procedure is described in above books.

The above silver halide emulsions can be chemically sensitized in a conventional manner, if desired. Chemical sensitizers include for example chloroaurate, auricchloride and like gold compounds as shown in U.S. Pats. Nos. 2,399,083, 2,540,085, 2,597,856 and 2,597,915; salts of noble metals such as platinum, palladium, iridium, rhodium and ruthenium as shown in U.S. Pats. Nos. 2,448,060, 2,540,086, 2,566,245, 2,566,263 and 2,598,079; sulfur compounds forming silver sulfide upon reaction with a silver salt, as shown in U.S. Pats. Nos. 1,574,944, 2,410,689, 3,189,458 and 3,501,313; stanous salts, amines and other reducing substances, as shown in U.S. Pats. Nos. 2,487,850, 2,518,698, 2,521,925, 2,521,926, 2,694,637, 2,983,610 and 3,201,254.

The photographic emulsion containing the hardener of the present invention can, if desired, be spectrally sensitized or supersensitized by the use of cyanine, merocyanine, carbocyanine and like cyanine dyes alone or combination, or in combination with styryl dyes.

Such dye sensitizing techniques arts are well known and are shown in U.S. Pats. Nos. 2,493,748, 2,519,001, 2,977,229, 3,480,434, 3,672,897, 3,480,434, 3,672,897, 3,703,377, 2,688,545, 2,912,329, 3,397,060, 3,615,635, 3,628,964, British Pats. Nos. 1,195,302, 1,242,588 and 1,293,862, German Pat. (OLS) Nos. 2,030,326 and 2,121,780, Japanese Pat. Nos. 4936/68, 14030/69 and 10773/68, U.S. Pat. Nos. 3,511,664, 3,522,052, 3,527,641, 3,615,613, 3,615,632, 3,617,295, 3,635,721, 3,694,217, British Pat. Nos. 1,137,580 and 1,216,203 and the like. The material(s) can freely be determined depending on the wave length range to be sensitized, sensitivity, end use objective and the like.

To the above photographic emulsion there can be added various compounds in order to prevent a reduction of sensitivity and the generation of fog during manufacturing, storage or treatment of the photographic materials. As such compounds many compounds are known, for example, 4-hydroxy-6-methyl-1,3,3a,7-tetrazaindene, 3-methyl-benzothiazole, 1-phenyl-5-mercaptotetrazole and like heterocyclic compounds, mercury containing compounds, mercapto compounds and metal salts. Examples of usable compounds are described in the following patents as well as in C. E. K. Mees, *The Theory of the Photographic Process*, 2nd edition, pp. 344–349, 1966 referring to the original literature; U.S. Pats. Nos. 1,758,576, 2,110,178, 2,131,038, 2,173,628, 2,697,040, 2,304,962, 2,324,123, 2,394,198, 2,444,605-8, 2,566,245, 2,694,716, 2,697,099, 2,708,162, 2,728,663–5, 2,576,536, 2,824,001, 2,843,491, 2,886,437, 3,052,544, 3,137,577, 3,220,839, 3,226,231, 3,236,652, 3,251,691, 3,252,799, 3,287,135, 3,326,681, 3,420,668, 3,622,339, British Pats. Nos. 893,428, 403,789, 1,173,609 and 1,200,188.

As gelatin to which the hardener of the present invention is applied there may be used any of the alkali treated gelatin obtained by immersion in an alkali bath (lime-treatment) before gelatin extraction, acid treated gelatin obtained by immersing in an acid bath and enzyme treated gelatin as described in Bull. Soc. Sci. Photo. Japan, No. 16, page 30, 1966. Further, the present hardener can be applied to the low molecular weight gelatin which is obtained by partial hydrolysis of gelatin through heating in a water bath or interaction with protenase.

The gelatin to which the hardener of the present invention is applied may, if desired, be substituted for in part by colloidal albumin, casein, cellulose derivatives such as carboxymethylcellulose and hydroxyethylcellulose, agar, sodium alginate, starch derivatives and like saccharide derivatives, and synthetic hydrophillic colloids such as polyvinyl alcohol, poly-N-vinyl pyrrolidone, polyacrylic acid copolymers, polyacrylamide and derivatives thereof. In addition, the gelatin may be substituted for by a gelatin derivative which is obtained by treating or reforming the amino, imino, hydroxy or carboxyl group contained as functional group in a gelatin molecule with a reagent having a radical capable of reacting with such functional groups, or may be substituted for by a graft polymerized gelatin in which a molecular chain of another polymeric substance is attached to gelatin. It is most preferred in accordance with the present invention that when gelatin is substituted for by one of the above materials, that the substitution be for no more than about to 50% by weight of the gelatin.

As the reagents for producing the above derivatives there may be mentioned for example, isocyanates, acid chlorides or acid anhydrides as shown in U.S. Pat. No. 2,614,928; acid anhydrides as shown in U.S. Pat. No. 3,118,766; bromoacetic acids as shown in Japanese Pat. No. 5514/64; phenylglycidyl ethers as shown in Japanese Pat. No. 26845/67; vinylsulfone compounds as shown in U.S. Pat. No. 3,132,945; N-allylvinylsulfonamides as shown in British Pat. No. 861,414; maleinimide compounds as shown in U.S. Pat. No. 3,186,846; acrylonitriles as shown in U.S. Pat. No. 2,594,293; polyalkylene oxides as shown in U.S. Pat. No. 3,312,553; epoxy compounds as shown in Japanese Pat. No. 26845/47; acid esters as shown in U.S. Pat. No. 2,763,739; and alkanesultones as shown in British Pat. No. 1,033,189.

Branched polymers which can be grafted to gelatin are described in many literature publications such as U.S. Pats. Nos. 2,763,625, 2,831,767 and 2,956,884, Polymer Letters 5 595 (1967), Photo. Sci. Eng. 9, 148(1965), J. Polymer Sci. A1 9, 3199(1971) and the like, and polymers or copolymers of vinyl monomers such as acrylic acid, methacrylic acid, or esters, amides, nitriles and the like derivatives thereof, or styrene, may be used. Particularly preferably are hydrophilic vinyl polymers compatible with gelatin to some extent, such as polymers or copolymers of acrylic acid, acrylamide, methacrylamide, hydroxyalkyl acrylate and hydroxyalkyl methacrylate.

In using the hardener of the present invention, the photographic emulsion layer or other layers may have incorporated therein synthetic polymer compounds, e.g., latex like water dispersable polymers of vinyl compounds, particularly compounds increasing the dimensinal stability of the photographic materials, alone or as a mixture (a mixture of different kinds of polymers), or in combination with hydrophilic water permeable colloids. Many such polymers are shown, for example, in U.S. Pats. Nos. 2,376,005, 2,739,137, 2,853,457, 3,062,674, 3,411,911, 3,488,708, 3,525,620, 3,635,715, 3,607,290, 3,645,740 and in British Pats. Nos. 1,186,699 and 1,307,373. Among these are generally used copolymers and homopolymers of monomers selected from the group consisting of alkyl acrylates, alkyl methacrylates, acrylic acid, methacrylic acid, sulfoalkyl acrylates, sulfoalkyl methacrylates, glycidyl acrylate, glycidyl methacrylate, hydroxyalkyl acrylates, hydroxyalkyl methacrylates, alkoxyalkyl acrylates, alkoxyalkyl methacrylates, styrene, butadiene, vinyl chloride, vinylidene chloride, maleic anhydride and itaconic anhydride. If desired, there may be used a graft type emulsion polymerization latex obtained by emulsion polymerizing the aforementioned vinyl compounds in the presence of a hydrophillic protective colloidal polymer compound.

In producing the photographic materials, the gelatin hardener of the present invention may be used in combination with a matting agent. As matting agents, there may be used particles of water insoluble organic or inorganic compounds, with an average particle size of 0.2 $\mu$ to 10 $\infty$, preferably 0.3 $\mu$ to 5$\mu$. Examples of organic compounds are water dispersable vinyl polymers such as polymethyl acrylate, polymethyl methacrylate, polyacrylonitrile, acrylonitrile-$\alpha$-methylstyrene copolymers, polystyrene, styrenedivinylbenzene copolymers, polyvinyl acetate, polyethylene carbonate, polytetrafluoroethylene; cellulose derivatives such as methyl cellulose, ethyl cellulose, cellulose acetate, cellulose acetate propionate; starch derivatives such as carboxy starch, carboxynitrophenyl starch, urea-formaldehyde-starch reaction products; and gelatin hardened with known hardeners and hollow microcapsules of hardened gelatin, that is as obtained by coacervate hardening. Examples of inorganic compounds are silicon dioxide; titanium dioxide; magnesium oxide; aluminum oxide; barium sulfate; calcium carbonate; silver chloride and silver bromide desensitized by known methods, glass and the like. The above matting agents may, if desired, be used as a mixture of two or more thereof.

In producing the photgraphic materials, the gelatin hardener of the present invention may be used in combination with one or more couplers. In this case, diffusion resistant couplers are incorporated to a silver halide emulsion layer. Examples of couplers are four-equivalent diketomethylene yellow couplers and two-equivalent diketomethylene yellow couplers, for example, compounds as shown in U.S. Pat. Nos. 3,415,652, 3,447,928, 3,311,476,and 3,408,194; compounds as shown in U.S. Pat. Nos. 2,875,057, 3,265,506, 3,409,439, 3,551,155 and 3,551,156; compounds as shown in Japanese Patent No. (OPI) No. 26133/72 and 66836/73; four-equivalent or two-equivalent pyrazolone magenta coupler and indazolone magenta couplers, for example, compounds as shown in U.S. Pat. Nos. 2,600,788, 2,983,608, 3,062,653, 3,214,437, 3,253,924, 3,419,391, 3,419,808, 3,476,560 and 3,582,322, Japanese Pat. No. 20636/70, Japanese Pat. No. (OPI) 26133/72; $\alpha$-naphthol type cyan coupler and phenol type cyan coupler, for example, compounds as shown in U.S. Pat. Nos. 2,474,293, 2,698,794, 3,034,892, 3,214,437, 3,253,924, 3,311,476, 3,458,315, 3,591,383, Japanese Pat. Nos. 11304/67 and 32461/69. In addition, there are used compounds as shown in U.S. Pat. Nos. 3,227,554, 3,297,445, 3,253,924, 3,311,476, 3,379,529, 3,516,831, 3,617,291, 3,705,801, German Pat. (OLS) No. 2,163,811.

To the photgraphic emulsion of the photgraphic materials, to which the hardener of the present invention is added or to be added, there may be added surface active agents alone or in mixture. Although such surface active agents are used as coating aids, they may also be used for other purposes, for example, for the purposes of emulsification and dispersion, sensitization, improvement of photographic properties, prevention of static charging and prevention of adhesion.

These surface active agents are classified as naturally occurring surface active agents such as saponin; non-ionic surface active agents such as those of alkylene oxide type, glycerine type and glycidol type; cationic surface active agents such as higher alkylamines, quaternary ammonium salts, pyridine and like heterocyclic compounds, phosphoniums and sulfoniums; anionic surface active agents containing acidic groups such as carboxylic acid, sulfonic acids, phosphoric acid, sulfonic acid ester and phosphoric acid esters; and amphoteric surface active agents such as amino acids, amino sulfonic acids, and sulfates or phosphates of amino alcohols.

Additional examples of useful surface active agents used are described not only in U.S. Pat. Nos. 2,271,623, 2,240,472, 2,288,226, 2,739,891, 3,068,101, 3,158,484, 3,201,253, 3,210,191, 3,294,540, 3,415,649, 3,441,413, 3,442,654, 3,475,174, 3,545,974; German Pat. (OLS) No. 1,942,665, British Pat. Nos. 1,077,317, 1,198,450 but also in texts such as Ryohei Oda, *Synthesis and Application of Surface-active Agents*, (Maki Publisher, 1964), A. W. Perry, *Surface Active Agents*, (Interscience Publication Incorporated, 1958). J. P. Sisley, *Encyclopedia of Surface-active Agents*, Vol. 2 (Chemical Publishing Company, 1964) and the like.

The photographic emulsions described above are coated on a planar substance which does not undergo substantial dimensional changes during processing, for example, hard supports such as glass, metal and ceramics, and flexible supports, depending on the objective.

Representative examples of flexible supports are include those generally used for photographic materials such as cellulose nitrate film, cellulose acetate film, cellulose acetate butyrate film, cellulose acetate propionate film, polystyrene film, polyethylene terephthalate film, polycarbonate film and laminates thereof; thin glass film; paper coated with baryta; paper coated or laminated with an $\alpha$-olefin polymer, particularly a polmer of an$\alpha$-olefin containing 2-10 carbon atoms, such as polyethylene, polypropylene and ethylene-butene copolymers; and a plastic film whose surface is coarsened to thereby improve adhesion to other polymeric substances and to improve the printability thereof.

Depending on the end use of the photographic materials, transparent or opaque suports can be used. The transparent supports can be color by the addition of dyes and for pigments. This has long been done in the production of X-ray films, and is shown in J. SMPTE 67, 296 (1958)

The opaque supports include not only those originally opaque ones such as paper, but also those obtained by adding to a transparent film a dye and/or pigment such as titanium dioxide, a surface treated plastic film as shown in Japanese Pat. No. 19068/72, and paper and plastic film which have been made completely light-shading by the addition of carbon black or dyes.

When the adhesion strength between the support and the photographic emulsion layer is insufficient, a subbing layer which has a good adhesion for both is provided. In order to further improve the adhesion, the surface of the support can be subjected to a pre-treatment such as a corona discharge, an ultraviolet ray irradiation or a flame treatment.

In using the hardener of the present invention, each layer of the photographic materials can be coated by various coating methods including dip coating, air knife coating, curtain coating, spray coating, extrusion coating using a hopper as described in U.S. Pat. No. 2,681,294, etc.; if desired, two or more layers can be simultaneously coated by methods as described in U.S. Pat. Nos. 2,761,791, 3,508,947, 2,941,898 and 3,526,528.

The present hardener can be used not only by adding it to the photographic materials but also by adding it to a processing solution. The addition amount is about 1 to about 1,000 milimoles, preferably 10 to 100 milimoles, per 1 liter of the processing solution. Most preferred examples of processing solutions to which the hardener of the present invention can be added include a prehardening solution, a developer solution, a fixing solution, etc.

Synthesis Examples of compounds used in the present invention and Examples of the present invention are given below. Unless otherwise indicated, in the following Synthesis Examples, all percentages are weight percentages.

SYNTHESIS EXAMPLE 1

Synthesis of Compound

To 88 grams of sodium hydrogen sulfite in 400 ml of water were added dropwise 131 g of $\beta$-chloroethanesulfonyl chloride and 88 g of sodium hydroxide in 240 ml of water simultaneously at about 5° C. After 30 minutes, 80 g of a 50% sulfuric acid aqueous solution was added dropwise thereto, and the mixture stirred for 1 hour at 5° C, followed by filtration. To the filtrate was dropwise added 57 g of acrylic acid in 100 ml of water, and the resulting mixture was allowed to stand for about 3 days while cooling at 10° C. The crystals precipitated were filtered off and recrystallized from water to give 109 g of white, crystalline $\beta$-($\beta$-chloroethanesulfonyl)propionic acid, m.p. 138°–9° C.

50 grams of $\beta$-($\beta$-chloroetthanesulfonyl)propionic acid and 150 ml of thionyl chloride were heated under refluxing for about 2 hours, excess thionyl chloride distilled off under reduced pressure, and the residue recrystallized from anhydrous benzene to give 46 g of white $\beta$-($\beta$-chloroethanesulfonyl)propionyl chloride, m.p. 73°–5° C.

13 grams of $\beta$-($\beta$-chloroethanesulfonyl)propionyl chloride was dissolved in 400 ml of acetone. To the resulting solution was added 8 g of N-hydroxysuccinimide, and 7 g of triethylamine in 70 ml of acetone was added dropwise with stirring at 0° C. After stirring for 3 hours at 0° C, the temperature raised to room temperature, and, after stirring for two hours at room temperature, the reaction mixture was concentrated under reduced pressure to ½ its original volume. The residue was poured into 1.5 liters of cold water, the crystals separated out filtered off and recrystallized from acetone to give 15 g of white crystalline objective compound, m.p. 165°–6° C.

| Elementary Analysis | C | H | N |
|---|---|---|---|
| Calculated (%) | 36.30 | 4.03 | 4.70 |
| Observed (%) | 36.35 | 4.14 | 4.84 |

SYNTHESIS EXAMPLE 2

(Synthesis of Compound 2)

13 grams of the succinimido ester of $\beta$-($\beta$-chloroethanesulfonyl)propionic acid obtained in Synthesis Example 1 was dissolved in 300 ml of acetone. To the resulting solution 5 g of triethylamine in 100 ml of acetone was added dropwise with stirring at 0° C, and the mixture was stirred for 5 hours at room temperature after dropwise addition. The reaction liquid was then concentrated to about half its original volume. To the residue was added 500 ml of cold water, and the crystals precipitated filtered off. The crystals were recrystallized from acetone to give 9.6 g of white crystals of the objective compound, m.p. 112°–4° C.

| Elementary Analysis | C | H | N |
|---|---|---|---|
| Calculated (%) | 41.38 | 4.21 | 5.36 |
| Observed (%) | 41.36 | 4.17 | 5.66 |

SYNTHESIS EXAMPLE 3

(Synthesis of Compound 4)

In a similar way as in Synthesis Example 1, 16.4 g of $\beta$-($\beta$-chloroethanesulfonyl)propionyl chloride was reacted with 6.7 g of N-methylacetohydroxamic acid, followed by recrystallization from acetone/hexane, to give 7 g of white crystals of the objective compound, m.p. 97°–100° C.

| Elementary Analysis | C | H | N |
|---|---|---|---|
| Calculated (%) | 35.40 | 5.15 | 5.15 |
| Observed (%) | 35.24 | 5.14 | 5.38 |

SYNTHESIS EXAMPLE 4

(Synthesis of Compound 5)

In a similar way as in Synthesis Example 2, 8.8 g of the N-methylacetamido ester of $\beta$-($\beta$-chloroethanesulfonyl)propionic acid was reacted with 3.6 g of triethylamine to give 5.4 g of white crystals of the objective compound, m.p. 68°–71° C.

| Elementary Analysis | C | H | N |
|---|---|---|---|
| Calculated (%) | 40.85 | 5.53 | 5.96 |
| Observed (%) | 40.93 | 5.79 | 6.13 |

SYNTHESIS EXAMPLE 5

(Synthesis of Compound 6)

19 grams of $\beta$-($\beta$-chloroethanesulfonyl)propionyl chloride, 3 g of paraformaldehyde and a small amount of anhydrous zinc chloride were heated for 30 minutes at 140° C. To the reaction mixture was added 300 ml of benzene at 50° C, followed by filtration. The mother liquid was concentrated, the crystals separated out after cooling filtered off and then recrystallized from benzene to give white crystals (7.3 g) of the objective compound, m.p. 73.5°–75° C.

| Elementary Analysis | C | H | N |
|---|---|---|---|
| Calculated (%) | 28.93 | 4.05 | 0 |
| Observed (%) | 28.83 | 4.28 | 0 |

SYNTHESIS EXAMPLE 6

(Synthesis of Compound 11)

11 grams of $\beta$-($\beta$-chloroethanesulfonyl)propionyl chloride and 3 g of acrylamide were heated for 15 minutes at 120° C, then the reaction liquid cooled to 80° C and 30 ml of chloroform was added to the reaction mixture. The crystals separated out were filtered off and recrystallized from methanol to give 8.7 g of white crystals of the objective compound, m.p. 115°–120° C.

| Elementary Analysis | C | H | N |
|---|---|---|---|
| Calculated (%) | 33.11 | 4.52 | 4.83 |
| Observed (%) | 33.31 | 4.64 | 5.04 |

SYNTHESIS EXAMPLE 7

(Synthesis of Compound 12)

This compound can also be obtained by removing hydrochloric acid from Compound 11 with triethylamine.

EXAMPLE 1

The compound of the present invention as shown in Table 1 was added to a 5% gelatin aqueous solution in an amount as shown in the following Table, and the resulting gelatin aqueous solution was divided into two portions. One portion was coated uniformly on a glass plate which had been subbed, in order to prepare a sample in which the thickness of the dry gelatin film was about 20 $\mu$. While storing this sample at 25° C, 55% RH, a part of the sample was taken off on the 1st, 7th and 14th day after coating in order to measure the melting temperature of the gelatin film in a 2 wt% sodium carbonate aqueous solution whose temperature rose 1° C every one minute starting at 20° C.

The sample stored for 14 days at 25° C, 55% RH was further stored for 2 days at 50° C (under accelerated aging conditions) in order to measure the melting temperature of the gelatin film in the same way as described above.

The remaining portion of the divided aqueous gelatin solution was kept at 40° C in order to observe the increase of viscosity of the aqueous solution. As is seen from the following Table, hardening proceeds smoothly after film formation with the compound of the present invention, and the compound of the present invention does not make it impossible to coat due to coagulating the aqueous gelatin solution.

Table 1

| Compound | Addition amount | Film melting temperature (° C) | | | Accelerated aging conditions | Solution Increase of viscosity |
| | | 1 day after coating | 7 days after coating | 14 days after coating | | |
|---|---|---|---|---|---|---|
| Control | 0 mmol/g gelatin | 33 | 33 | 33 | 35 | Not observed |
| Compound 1 | 0.03 | 79 | 79 | 79 | 80 | Practical increase of viscosity not observed |
| Compound 2 | 0.03 | 76 | 82 | 82 | 83 | " |
| Compound 4 | 0.03 | 72 | 75 | 76 | 76 | " |
| Compound 5 | 0.03 | 69 | 70 | 71 | 72 | " |
| Compound 6 | 0.03 | 75 | 76 | 76 | 76 | " |
| Compound 12 | 0.03 | 75 | 80 | 80 | 82 | " |
| $\beta$-methylglutaraldehyde | 0.03 | 55 | 68 | 75 | 78 | Gelatin coagulated |

EXAMPLE 2

The compound of the present invention was added in an amount as shown in Table 2 to a silver halide photographic emulsion containing 120 g of gelatin and 80 g of silver bromide per 1 kg of the emulsion, and the thus prepared emulsion was coated uniformly on a cellulose triacetate base having a subbing layer so that the thickness of the dry gelatin film was about 10 $\mu$, followed by drying.

The obtained film sample was wedge-exposed, developed for 8 minutes at 20° C with D-76 developer, and then subjected to sensitometry after fixing, washing with water and drying, in order to determine sensitivity and fogging.

Further, the melting temperature of the emulsion film in 2% sodium carbonate solution was determined (in accordance with the method in Example 1) for a sample stored for 7 days after coating. The results are given in Table 2.

As is seen from Table 2, the compounds of the present invention provide sufficient film strength to permit practical use and do not adversely affect photographic properties.

Table 2

| Compound | Addition amount mmole/g gelatin | Film melting temperature (° C) (7 days after coating) | Immediately after coating Relative sensitivity | Fog | Accelerated aging conditions (50° C, 2 days) Relative Sensitivity | Fog |
|---|---|---|---|---|---|---|
| Control | 0 | 33 | 100 | 0.05 | 100 | 0.35 |
| Compound 1 | 0.05 | >90 | 96 | 0.05 | 98 | 0.08 |
| Compound 3 | 0.05 | >90 | 92 | 0.04 | 96 | 0.10 |
| Compound 7 | 0.05 | >90 | 93 | 0.04 | 93 | 0.10 |
| Compound 8 | 0.05 | 90 | 95 | 0.04 | 95 | 0.11 |
| Compound 12 | 0.05 | >90 | 97 | 0.04 | 98 | 0.10 |
| β-methylglutaraldehyde | 0.05 | 76 | 83 | 0.06 | 85 | 1.77 |

EXAMPLE 3

A silver iodobromide emulsion containing 3.0 mole% of silver iodide was after ripened in the presence of sodium thiosulfate and gold salt so that maximum sensitivity was obtained, to prepare a high sensitivity negative emulsion.

1-(2',4',6'-trichlorophenyl)-3-[3'''-(2''',4'''-di-t-amylphenoxyacetamido)benzamido]-5-pyrazolone was dissolved in a mixture of dibutyl phthalate and tricresyl phosphate, and this solution was dispersed in a solution of gelatin using sorbitan monolaurate, Turky red oil and sodium dodecylbenzenesulfonate as emulsifying agents to prepare an o/w coupler emulsion. This coupler emulsion was added to the above emulsion. The thus prepared emulsion was divided equally, and to one portion was added Compound 2 of the present invention and to the other was added Compound 12 of the present invention in an amount of 0.07 m mole per 1g of dry gelatin, respectively. Each emulsion was coated on a cellulose triacetate base having a subbing layer so that the thickness of the dry gelatin film was about 10 μ, followed by drying, to prepare a magenta monolayer color film for experimental use. This color film was wedge-exposed, color developed with a developer containing as a developing agent 4-amino-3-methyl-N-ethyl-β-hydroxyethylaniline sesquisulfate monohydrate, and the coloring characteristics were investigated by sensitometry. It was found that the compound of the present invention did not adversely affect the coloring characteristics of the coupler and did not generate a color stain.

While the invention has been described in detail and with reference to specific embodiments thereof, it will be apparent to one skilled in the art that various changes and modifications can be made therein without departing from the spirit and scope thereof.

What is claimed is:

1. A method of hardening gelatin which comprises adding thereto a compound of the following general formula (I):

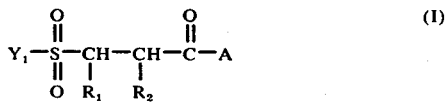

in which $Y_1$ is $CH_2$=CH—, $ClCH_2$—$CH_2$—, $BrCH_2$—$CH_2$—, $CH_3COO$—$CH_2CH_2$— or $ClCH_2COO$—$CH_2CH_2$—, $R_1$ and $R_2$ are H or $CH_3$, but both of them are not $CH_3$ at the same time, and A is one of the following groups:

(1) esters

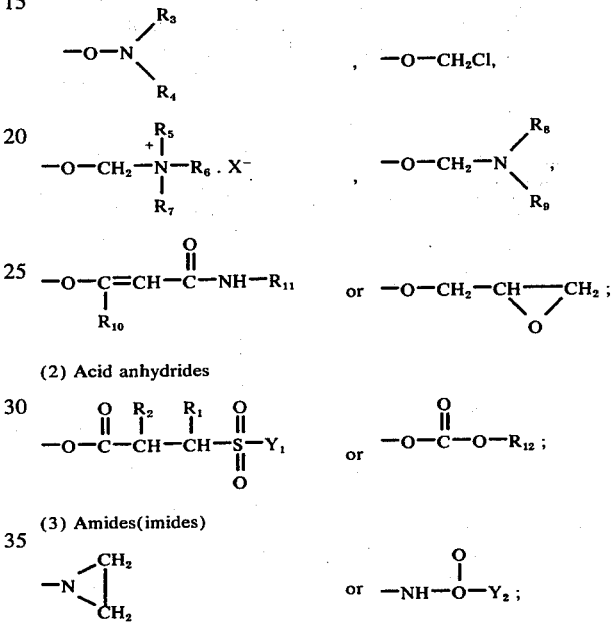

(2) Acid anhydrides (3) Amides(imides)

in which both $R_3$ and $R_4$ are acyl groups or at least one of them is an acyl group other than when $R_3$ and $R_4$ form a benzotriazole ring, and when one or $R_3$ and $R_4$ is an acyl group, the other is H or an alkyl group containing at most 4 carbon atoms; and wherein in any case, $R_3$ and $R_4$ may form a saturated or unsaturated carbocyclic or heterocyclic ring in combination with the nitrogen atom to which they are attached; $R_5$, $R_6$ and $R_7$ are alkyl groups containing at most 4 carbon atoms, and may form a saturated or unsaturated ring, or may form a bicyclo ring; $X^-$ is an acid anion; $R_8$ and $R_9$ are a saturated or unsaturated carbocyclic or heterocyclic ring in combination with the nitrogen atom to which they are attached; $R_{10}$ is an alkyl or aryl group containing at most 6 carbon atoms; $R_{11}$ is an alkyl group containing at most 3 carbon atoms; $R_{12}$ is an alkyl, aryl or aralkyl group containing at most 7 carbon atoms; and $Y_2$ is $CH_2$=CH—, $ClCH_2$—$CH_2$—, Br—$CH_2$—$CH_2$—, $CH_3COO$—$CH_2CH_2$—, or $ClCH_2COO$—$CH_2CH_2$—.

2. The method of claim 1, wherein $R_8$ and $R_9$ are residues which form succinimide, maleninimide or phthalimide in combination with the nitrogen atom to which they are attached.

3. The method of claim 1, wherein in general formula I. $Y_1$ is $CH_2$=CH— or $ClCH_2CH_2$—, $R_1$ and $R_2$ are H, and A is either 1, 2 or 3 given below:

(1) Esters

-continued

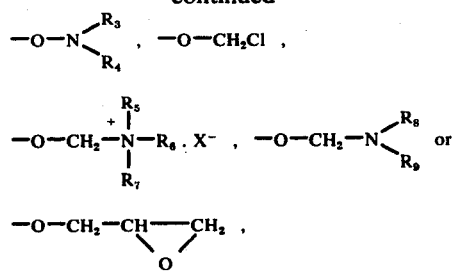

where $R_3$–$R_9$ and $X^-$ have the same meanings as in general formula (I);
2. Acid anhydrides as set forth in the general formula (I);
3. Amides (imides) as set forth in the general formula (I).

4. The method of claim 3, wherein in general formula (I) $Y_1$ is $CH_2=CH-$ or $ClCH_2CH_2-$, $R_1$ and $R_2$ are H, and A is either (1), (2) or (3) as set forth below:
 1. Esters as set forth in claim 3;
 2. An acid anhydride of the formula:

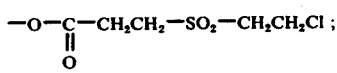

3. Amides (imides) of the formula:

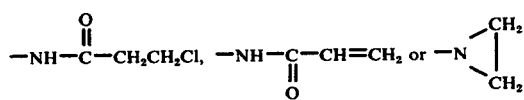

5. The method of claim 1, where in general formula (I) $Y_1$ is $CH_2=CH-$ or $ClCH_2CH_2-$, $R_1$ and $R_2$ are H, and A is

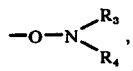

where $R_3$ and $R_4$ have the same meaning as in general formula (I);

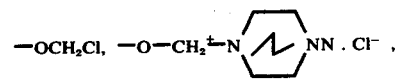

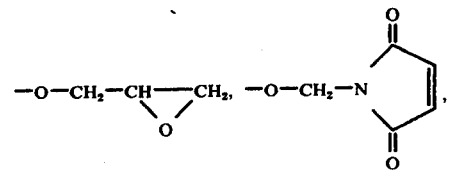

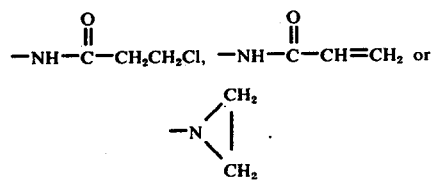

6. The method of claim 1, wherein in general formula (I) $Y_1$ is $CH_2=CH-$ or $ClCH_2CH_2-$, $R_1$ and $R_2$ are H, and A is

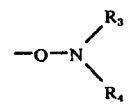

where $R_3$ and $R_4$ are the same as in general formula (I) or

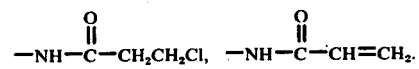

7. The method of claim 1, wherein said hardener is added to said gelatin in an amount of from about 0.05 to about 20 weight %, based on dry gelatin.

8. The method of claim 2, wherein said hardener is added to said gelatin in an amount of 0.1 to 10 weight %, based on dry gelatin.

* * * * *